US008151635B2

(12) United States Patent
Ivanov et al.

(10) Patent No.: US 8,151,635 B2
(45) Date of Patent: Apr. 10, 2012

(54) METHODS AND DEVICE FOR FAST CREATION OF FLUID INTERFACES AND USE OF THIS DEVICE FOR DETERMINATION OF LIQUID-LIQUID AND LIQUID-GAS INTERFACIAL PROPERTIES

(75) Inventors: Ivan B. Ivanov, Sofia (BG); Krastanka G. Marinova, Sofia (BG); Vassil Vulchev, Sofia (BG); Dora T. Dimitrova, Vratza (BG); Krasimir D. Danov, Sofia (BG); Nikolai D. Denkov, Sofia (BG); Stoyan Russev, Sofia (BG); Lyudmil Lyutov, Sofia (BG); Nikola Alexandrov, Sofia (BG)

(73) Assignee: Kruess GmbH Wissenschaftliche Laborgeraete, Hamburg (DE)

( * ) Notice: Subject to any disclaimer, the term of this patent is extended or adjusted under 35 U.S.C. 154(b) by 568 days.

(21) Appl. No.: 12/292,692

(22) Filed: Nov. 24, 2008

(65) Prior Publication Data
US 2009/0133480 A1 May 28, 2009

(30) Foreign Application Priority Data
Nov. 24, 2007 (DE) .......................... 10 2007 056 669

(51) Int. Cl.
*G01N 13/02* (2006.01)
(52) U.S. Cl. .................. 73/64.52; 73/64.48; 73/64.51
(58) Field of Classification Search ............... 73/61.48, 73/61.51, 61.52, 64.48, 64.51, 64.52
See application file for complete search history.

(56) References Cited

U.S. PATENT DOCUMENTS

| | | | | | |
|---|---|---|---|---|---|
| 2,473,553 | A | * | 6/1949 | Stokes | 73/64.52 |
| 3,048,999 | A | * | 8/1962 | Robert | 73/64.48 |
| 3,483,737 | A | * | 12/1969 | Schoettle | 73/64.52 |
| 3,765,227 | A | * | 10/1973 | Campbell et al. | 73/64.51 |
| 3,913,385 | A | * | 10/1975 | Jobe | 73/61.43 |
| 4,196,615 | A | * | 4/1980 | Davis | 73/64.52 |
| 4,361,032 | A | * | 11/1982 | Lessnig et al. | 73/64.52 |
| 4,416,148 | A | * | 11/1983 | Klus et al. | 73/64.51 |
| 4,697,451 | A | * | 10/1987 | Matteson | 73/64.52 |
| 4,800,750 | A | * | 1/1989 | Enhorning | 73/64.48 |
| 4,874,426 | A | * | 10/1989 | Honda | 73/64.48 |
| 4,942,760 | A | * | 7/1990 | Almeida | 73/64.48 |
| 4,953,389 | A | * | 9/1990 | Schurch | 73/64.48 |
| 5,137,352 | A | * | 8/1992 | Blitshteyn et al. | 356/138 |
| 5,218,841 | A | * | 6/1993 | Hool | 73/64.52 |
| 5,269,176 | A | * | 12/1993 | Hool | 73/64.52 |
| 5,394,740 | A | * | 3/1995 | Schramm et al. | 73/64.48 |
| 5,479,816 | A | * | 1/1996 | Richou et al. | 73/64.48 |

(Continued)

FOREIGN PATENT DOCUMENTS
DE 10 2004 040 3 2/2006

OTHER PUBLICATIONS

M. Hoorfar et al., "Recent Progress in Axismmetric Drop Shape Analysis (ADSA)", Advances in Colloid and Interface Science, vol. 121, 2006, pp. 25-49.

(Continued)

*Primary Examiner* — David Rogers
(74) *Attorney, Agent, or Firm* — Staas & Halsey LLP (57) ABSTRACT

Methods for fast fresh surface formation between two fluids as well as a device employing this method to measure dynamic or equilibrium interfacial tension between the fluids.

9 Claims, 4 Drawing Sheets

(a) (b) (c) (d)

U.S. PATENT DOCUMENTS

| | | | | | |
|---|---|---|---|---|---|
| 5,542,289 | A | * | 8/1996 | Hool et al. | 73/64.52 |
| 5,615,276 | A | * | 3/1997 | Lin et al. | 382/100 |
| 5,637,467 | A | * | 6/1997 | Meltzer | 435/7.9 |
| 5,661,234 | A | * | 8/1997 | Gerits et al. | 73/64.48 |
| 6,085,577 | A | * | 7/2000 | Christensen et al. | 73/64.51 |
| 6,832,506 | B1 | * | 12/2004 | Mason et al. | 73/64.53 |
| 7,155,962 | B2 | * | 1/2007 | Knebel et al. | 73/64.52 |
| 7,481,097 | B2 | * | 1/2009 | Schumann et al. | 73/64.51 |
| 7,779,672 | B2 | * | 8/2010 | Robin | 73/29.01 |
| 2004/0177680 | A1 | * | 9/2004 | Skogo et al. | 73/64.51 |
| 2008/0173076 | A1 | * | 7/2008 | Robin | 73/61.78 |
| 2009/0309908 | A1 | * | 12/2009 | Basarah et al. | 347/10 |

OTHER PUBLICATIONS

D. Möbius et al., Table of Contents of "Novel Methods to Study Interfacial Layers", Elsevier, 2001, pp. vii-ix.

D. Möbius et al, Table of Contents of "Drops and Bubbles in Interfacial Research", Elsevier, 1998, p. xi.

Stanislow S. Dukhin et al., Table of Contents of "Dynamics of Adsorption at Liquid Interfaces", Elsevier, 1995, pp. vii-xv.

Arthur W. Adamson et al., Table of Contents of "Physical Chemistry of Surfaces", Sixth Edition, John Wiley & Sons, Inc., 1997, pp. vii-xvi.

Y. Rotenberg et al., "Determination of Surface Tension and Contact Angle from the Shapes of Axisymmetric Fluid Interfaces", Journal of Colloid and Interface Science, vol. 93, No. 1, May 1983, pp. 169-183.

P. Cheng et al., "Automation of Axisymmetric Drop Shape Analysis for Measurements of Interfacial Tensions and Contact Angles", Colloids and Surfaces, vol. 43, 1990, pp. 151-167.

Shi-Yow Lin et al., "Diffusion-Controlled Surfactant Adsorption Studied by Pendant Drop Digitization", AIChe Journal, vol. 36, No. 12, Dec. 1990, pp. 1785-1795.

L.G. Cascão Pereira et al., "Dilatational Rheology of BSA Conformers at the Air/Water Interface", Langmuir, vol. 19, 2003, pp. 2349-2356.

B. Song et al., "Determination of Interfacial Tension from the Profile of a Pendant Drop Using Computer-Aided Image Processing", Journal of Colloid and Interface Science, vol. 184, 1996, pp. 77-91.

A. Passerone et al., "A New Experimental Method for the Measurement of the Interfacial Tension between Immiscible Fluids at Zero Bond Number", Journal of Colloid and Interface Science, vol. 146, No. 1, Oct. 1, 1991.

T. Horozov et al., "A Local Approach in Interfacial Rheology: Theory and Experiment", Proc. First World Congress in Emulsion, Paris, 1993, pp. 3-20-137/01 to 3-20-137/06.

K.-D. Wantke et al., "Calculation of the Elasticity of Fluid Boundary Phases with the Oscillating Bubble Method", Journal of Colloid and Interface Science, vol. 159, 1991, pp. 28-36.

C.A. Macleod et al., "A Growing Drop Technique for Measuring Dynamic Interfacial Tension", Journal of Colloid and Interface Science, vol. 160, 1993, pp. 435-448.

R. Nagarajan et al., "Measurement of Dynamic Interfacial Tension by an Expanding Drop Tensiometer", Journal of Colloid and Interface Science, vol. 159, 1993, pp. 164-173.

X. Zhang et al., "Measurement of Dynamic Surface Tension by a Growing Drop Technique", Journal of Colloid and Interface Science, vol. 168, 1994, pp. 47-60.

T. Horozov et al., "A Novel Fast Technique for Measuring Dynamic Surface and Interfacial Tension of Surfactant Solutions at Constant Interfacial Area", Journal of Colloid and Interface Science, vol. 219, 1999, pp. 99-109.

T. Horozov et al., "Adsorption Kinetics of Some Polyethylene Glycol Octylphenyl Ethers Studied by the Fast Formed Drop Technique", Journal of Colloid and Interface Science, vol. 222, 2000, pp. 146-155.

N. C. Christov et al., "Maximum Bubble Pressure Method: Universal Surface Age and Transport Mechanisms in Surfactant Solutions", Langmuir, vol. 22, 2006, pp. 7528-7542.

* cited by examiner

METHODS AND DEVICE FOR FAST CREATION OF FLUID INTERFACES AND USE OF THIS DEVICE FOR DETERMINATION OF LIQUID-LIQUID AND LIQUID-GAS INTERFACIAL PROPERTIES

CROSS REFERENCE TO RELATED APPLICATIONS

This application is based on and hereby claims priority to German Patent Application No. 10 2007 056 669.9, filed on Nov. 24, 2007, the contents of which are hereby incorporated by reference.

BACKGROUND

The invention relates to methods and a device for fast creation of fluid interfaces and use of this device for the determination of liquid-liquid and liquid-gas interfacial properties.

The value of the equilibrium or dynamic ST/IFT of liquids determines processes like wetting, spreading, foaming, emulsification, coalescence, etc. The adsorption to a surface and the rate of adsorption directly affect the dynamic surface tension and are especially important for foaming and emulsification. The rate of adsorption of the surfactants on newly formed surfaces and interfaces depends on several factors among which are: type and bulk concentration of the surfactant, electrolyte concentration, temperature, diffusivity, hydrodynamic conditions, etc.

Many experimental methods for measurement of the equilibrium and dynamic ST/IFT exist. More recent reviews can be found in several books [1-4]. These methods differ by (i) the procedure of formation of the interface as well as (ii) by the technique of determination of the ST/IFT. The following sections shortly describe the procedures and the techniques and show drawbacks of the currently known methods and devices and their improvements by the claims applied for in this application:

(i) Formation of Interface

In principle, every method of formation of a new interface can be used for measuring both equilibrium and dynamic ST/IFT, provided that the time for surface formation can be regulated to be much shorter than the characteristic time of adsorption. The most widely used methods, Wilhelmy plate, du Noüy ring, Pendant and Sessile drops in their regular application do not meet this requirement and can be used for studying only very slow kinetics of adsorption. The methods based on drop or bubble formation by pushing a liquid or gas through a fluid to create a fresh interface are much faster. The most widely used methods of this kind are the Bubble Pressure Method (BPM) and the Drop Volume Method (DVM). In both methods the area and the shape of the interface change significantly during the measurement, which creates problems with the data interpretation and decreases the precision of calculation of the ST/IFT. In the methods described in claims 1 to 3 of this patent, the drop/bubble is formed for very short time and practically does not change its size during the measurement.

(ii) Determination of the ST/IFT

There are two main techniques for obtaining data and calculating the IFT/ST with drops and bubbles. The first technique, known as "Axisymmetric Drop Shape Analysis" (ADSA), uses the acquired shape of the drop/bubble surface. This technique is applicable only to deformed drops or deformed bubbles. The main idea of the method is that the shape of any fluid surface/interface under gravity is generally governed by the balance between the gravity and the capillary force. Under equilibrium conditions the mathematical description is given by the Young-Laplace equation:

$$\Delta P = \sigma(1/R_1 + 1/R_2),$$

where $\sigma$ is the interfacial tension, $R_1$ and $R_2$ are the principle radii of curvature and $\Delta P$ is the pressure difference across the drop interface. If gravity is the only external force then $\Delta P$ is given by $$\Delta P = \Delta P_0 + \Delta \rho g z,$$

where $\Delta P_0$ is the pressure difference at a reference plane (usually it is the plane passing through the apex of the drop/bubble), $\Delta \rho$ is the density difference between the fluids in the inner phase and the surrounding media, g is the acceleration due to gravity and z is the vertical coordinate of the drop/bubble generatrix, measured from the reference plane. The numerical solution of the equation allows obtaining the ST/IFT from the fit of the bubble/drop shape. This method has been widely applied for almost 20 years already [1-10]. There are also some apparatuses commercially available based on it (e.g. DSA10, DSA100, EasyDrop by Krüss, GER; FTA200, FTA2000 by First Ten Angstroms, USA; CAM 100, CAM 200 by KSV, Finland; ODT200, HFDT 500, by TECLIS-I.T.CONCEPT, France; PAT-1 by Sinterface, GER; OCA10, OCA20 by Dataphysics, GER). The ADSA has some requirements restricting its application. The formed drop/bubble must be large and deformed enough (the shape factor, or Bond number must be greater than e.g. 0.4 [9, 10]) in order to obtain the value of the IFT/ST with a satisfying accuracy, e.g. better than 0.1 mN/m. The Bond number is defined as $$Bo = \Delta \rho g R^2 / \sigma,$$

where R is the radius at the apex of the drop/bubble. Frequently it is not possible to achieve a high precision because:
 large drops especially with a low IFT are not easily kept attached to the capillary tip;
 large drops are subject to considerable mechanical vibrations;
 no satisfactory drop deformation can be achieved for interfaces between fluids with small density difference.

The second commonly used technique for determination of the ST/IFT is the Capillary Pressure Method (CPM). This technique is applicable only to spherical drops or bubbles. The method is based on measuring the pressure difference PC across a spherical drop interface with known radius of curvature R. The Young-Laplace equation in the form $$P_c = 2\sigma/R$$

is used to determine the value of the ST/IFT $\sigma$. When applying CPM in fact one measures a pressure difference P, which is sum of two components:

$$P = P_c + P_0,$$

where $P_0$ comprises all other contributions unrelated to the ST/IFT. The hydrostatic contribution depends on the relative position of the drop/bubble and the membrane of the pressure detector and the liquid density. The measured total pressure signal P often includes other constant additions (offsets of the electronics, etc.), which can be assigned to the term $P_0$. Usually the drop/bubble radius R is determined from digitized images obtained by video camera. The method has been applied for more than 15 years already [11-19] (for reviews see [1, 2]) but mostly in laboratory setups for research purposes. Commercial instruments using this method have appeared in the last two years (EDM/ODM-Module for DSA100, Krüss, GER; DPA-1 for PAT-1, Sinterface, GER).

The module produced by Krüss [18], is used for surface rheology characterization along with surface tension measurements.

There are two peculiarities of the CPM which are the main reasons for its rare application so far:
- the requirement of a spherical shape of the drop makes the method applicable under gravity for low Bond numbers only (Bo<0.1), which is fulfilled with small drop/bubble radius (e.g. smaller than 0.5 mm), or with systems with a small density difference of the fluids forming the interface [1, 2, 11-19]. That is why instruments based on this method have been constructed for use under microgravity conditions [2].
- the measurement by pressure detection relies on complex and time-consuming calibration procedures for the determination of $P_0$, which sometimes leads to lack of accuracy.

SUMMARY

Both procedures for determination of the ST/IFT could be taken up as complementary, as far as they are suitable for different ranges of the Bond number. That is why it is desirable to develop an improved device according to our claims, which combines these procedures and thereby covers a wider range of practical cases. Therefore the other aim of the invention is a device which not only implements new methods for interface formation but also allows using the two known measurement techniques, ADSA and CPM. In addition, with the proposed methods and the new device one can realize some other known methods for surface formation. The proposed new method and the device according to the claims are described in the next section.

BRIEF DESCRIPTION OF THE DRAWINGS

FIG. 1: Sketch of the measuring device.
- (5) capillary tube, e.g. steel needle, which is connected to the injection module (6) and the pressure detector (12); on the tip of the capillary a drop/bubble (1) is formed
- (6) injection module, e.g. a motorized syringe
- (7) illumination
- (8) optical lenses
- (9) imaging component converting optical image information into electronic signals, e.g. video camera with digital output or analog video camera connected to an image digitizing device like a frame grabber or other video analog-to-digital converters
- (10) device control box with electronics, through which the device is connected to the computer (11); this control box comprises drivers for the injection module (6) and illumination (7), analog-to-digital converter for the signal from the pressure detector (12); the control box ensures synchronization between video and pressure signals
- (11) computer with special application software installed
- (12) pressure detector
- (13) cuvette with optical windows (optional element) containing the outer phase (2).

FIG. 2: Sketch of an exemplary procedure for Protected Drop Method (PDM)
  a) Formation of a plug of pure liquid (3a) and atmospheric air (3b).
  b) Immersion of the capillary (5) in a surfactant solution (2).
  c) Pushing the inner liquid (1) with the plug (3a and 3b) out of the capillary.
  d) Plug release and new interface formation.

FIG. 3: Sketch of an exemplary procedure for Hidden Drop Method (HDM)
  a) Formation of a plug of pure liquid (3a) and atmospheric air (3b).
  b) Immersion of the capillary (5) in a surfactant solution (2).
  c) Pushing the inner liquid (1) with the plug (3a and 3b) toward the tip of the capillary.
  d) Part of the pure liquid component (3a) of the plug remains inside the capillary.
  The clean interface is exposed to the adsorption.

FIG. 4: Sketch of the Protected Bubble Method (PBM)—formation of a bubble using small gas volume. The preliminary preparation of the plug is analogous to one shown in FIGS. 2a and 3a and is not shown in the figure. The next steps are:
  a) Immersion of the capillary in a surfactant solution (2).
  b) The injection module drives the inner liquid until part of the gaseous inner phase (1) is released as one or more bubbles (3b).
  c) The residual gas forms bubble with fresh surface.

DETAILED DESCRIPTION OF THE INVENTION

The invention proposes three new methods for the creation of a fresh surface in order to measure the equilibrium and dynamic ST/IFT, realized by a single device. These methods are described in detail below:
  A) Protected Drop Method (PDM),
  B) Hidden Drop Method (HDM),
  C) Protected Bubble Method (PBM).

The PDM can be used for formation of either spherical or deformed drop. Whenever necessary to distinguish between these two cases the abbreviation PDM will be followed by an extension SD (for spherical drop), DD (for deformed drop), or DB (for deformed bubble). The Hidden Drop Method can only be used for spherical drops. The Protected Bubble Method can only be used for deformed bubbles.

Two known techniques for the determination of the ST/IFT (ADSA and CPM) can be used with the device, which comprises (FIG. 1):
  a capillary tube (5), to which tip a drop/bubble is attached (1), and which is connected to a pressure detector (12) and to an injection module (6), which controls the fluid in the inner volume;
  an optical imaging system, typically comprising an illumination (7), optical lenses (8), and an image detection system (9), e.g. video camera and video A/D-converter;
  electronics (10) and computer (11) with software which controls the device, analyzes drop shapes and pressure signals, if needed, and determines the ST/IFT.
  a glass cuvette (13) with optical windows, used as a container for the outer fluid phase (2).

Figure 1:
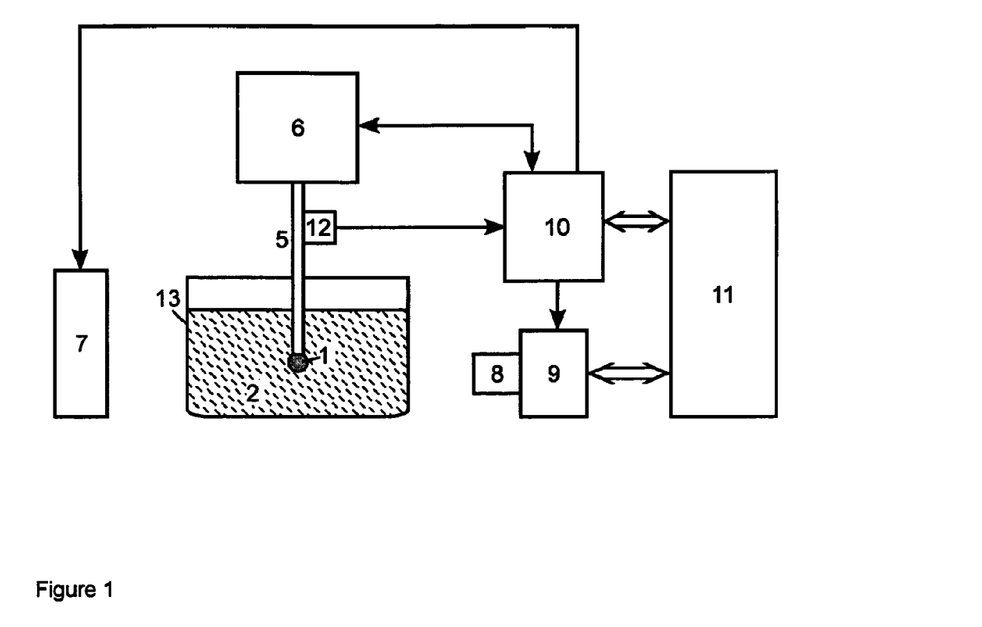

As a base for the implementation of the automated injection module (6) and optical system (7, 8 and 9) one could use e.g. DSA100 instrument by Krüss, GER. The injection module (6) represents a precise dosing system, based on a motorized syringe. The electronics (10) controls the syringe and provides different rates and precise dosing of the fluid(s) moving through the capillary according to the commands from the computer (11). A glass or metal needle can be used for a capillary (5).

The inner volume of the system comprises the syringe volume, the capillary volume, the volume of the connecting parts and the dead volume of the pressure detector. If it is desirable to use a small volume of the inner phase to form the new surface, the larger amount of the inner volume can be filled with a pure liquid in advance which is immiscible with the liquid used as the inner phase. Then the inner phase fluid is filled by using a quantity slightly larger than necessary to form a drop at the capillary tip. In the figures designations (1) and (2) stand for the inner (inside the drop/bubble) and outer phases respectively, which form the new interface, and (4) stands for the inert filling liquid.

The illumination (7), the capillary tube (5) and the camera (9) with lenses (8) are aligned in such a way that the drop/bubble (1) under examination is backlighted. The pressure detector is placed in contact with liquid media and has a suitable pressure range. All elements of the system are firmly attached to a solid frame.

The feature common to all new methods for fresh surface creation is the use of a fluid plug (denoted as (3) hereafter). The plug initially separates the fluid phases and ensures a pure surface of the fluid, which will finally come into contact with the surfactant solution. After removing the plug, the investigated phases form a common interface and the adsorption begins. The plug can be simple (of one fluid) or composite (of several fluids, denoted as 3a, 3b, etc.). The role of the single plug can also be performed by a small quantity of the inner phase, released as one or several drops or bubbles prior to the formation of the final drop or bubble. The different possibilities are described in detail in sections A-C below.

A. Protected Drop Method (PDM).

Figure 2:
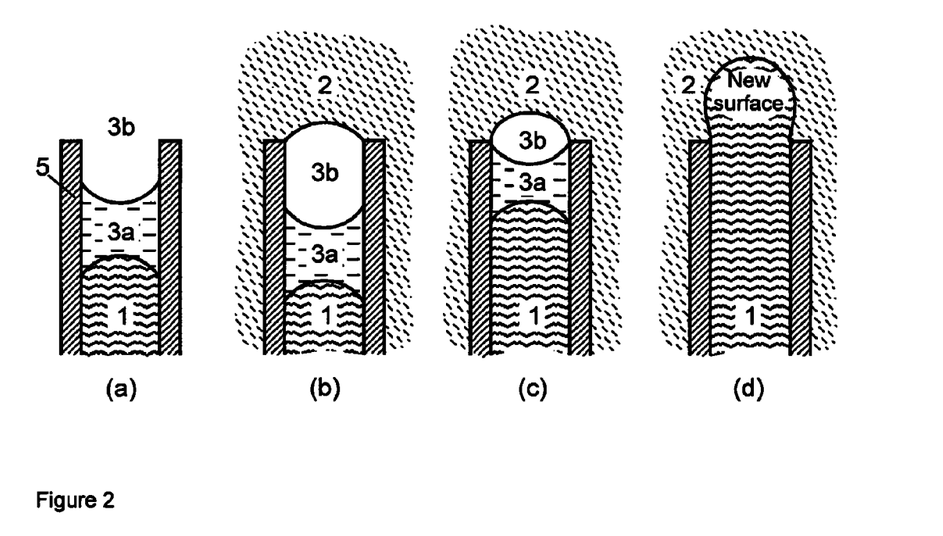

The outer phase (2) is placed in a glass cuvette with optical windows (13) in FIG. 1. The drop formation procedure consists of several steps, which are illustrated with an example in FIG. 2:

In step (a) small volumes, e.g. 0.1 to 100 microliters, first of pure liquid (3a) of the outer phase and afterwards air (3b) are sucked in (FIG. 2a). This could be achieved by dipping the capillary tip into a vessel with pure liquid and sucking in predetermined volume using the motorized syringe. After pulling out the capillary, a small volume of air is additionally sucked in.

In step (b) the capillary with the inner phase (1) and with the plug (3a and 3b) is immersed into a cuvette containing the outer phase with the surfactant (2), see FIG. 2b. The plug prevents the adsorption of the surfactant on the surface of the inner phase.

In step (c) pressure is applied on the inner content by means of the injection module. The inner phase and the plug are pushed out; during the plug release the gaseous component of the plug forms one or more bubbles (FIG. 2c). The amount of inner phase to be pushed out depends on what drop shape we want: small amount leads to spherical shape and large amount—to deformed drop.

In step (d) the inner (1) and the outer (2) phases come into contact and form a fresh interface (FIG. 2d).

From that time on the adsorption on the new interface starts.

The interfacial tension is determined by ADSA or CPM for deformed or spherical drop respectively.

For formation of pendant deformed drop the investigated fluid system may require a particular shape of the capillary tube. If the inner phase, say oil, has lower density than the outer phase, say an aqueous solution of a surfactant, the capillary (5) in FIG. 1 might be curved to point upward. In the opposite case it might point downwards.

The time for the formation of a spherical drop is shorter than for a deformed one, but usually the precision of the ADSA is better than CPM. The creation of a deformed drop is used in cases when a better precision of the ST/IFT values is preferred to the speed of drop formation. Both types of drops could be obtained by suitable settings for the working sequence for the injection module.

B. Hidden Drop Method (HDM)

Figure 3:
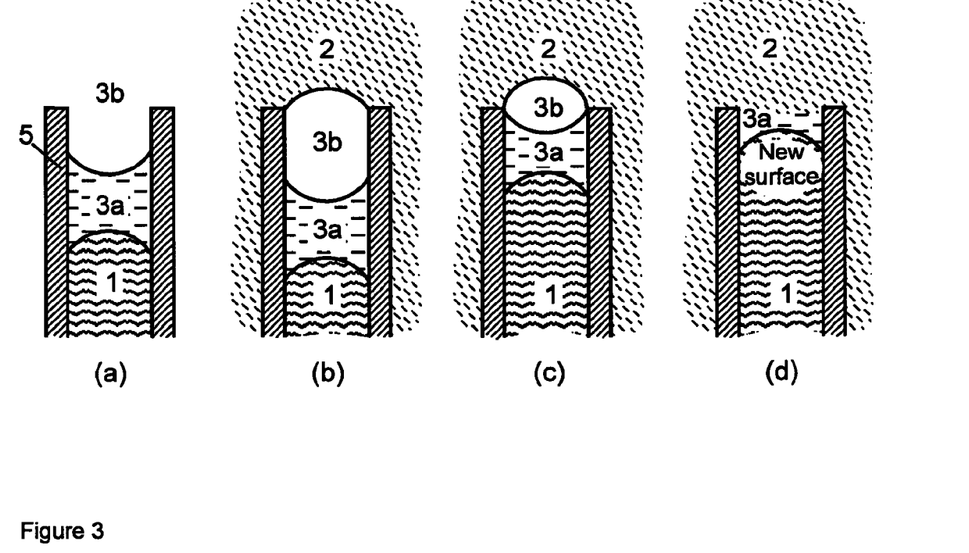

Basically, this is the same method as PDM, but with a different step (c). The volume of the inner phase pushed out by the injection module is set so that only part of the plug, i.e. the air bubble (3b) in FIG. 3, is released through the capillary orifice. Then, the pure liquid plug or part of it (3a) remains between the inner phase (1) and the outer phase (2), (FIG. 3d). The surfactant diffuses across it before adsorbing to the interface between the inner phase and the pure liquid plug. As a result, the adsorption on the inner surface starts at absolutely pure interface and the decrease of the interfacial tension starts several seconds after the hidden drop was formed (see FIG. 3d). The CPM is used to obtain the dynamic IFT. The determination of the radius of the curved drop surface requires the use of a transparent (e.g. glass) capillary.

C. Protected Bubble Method (PBM).

Figure 4:
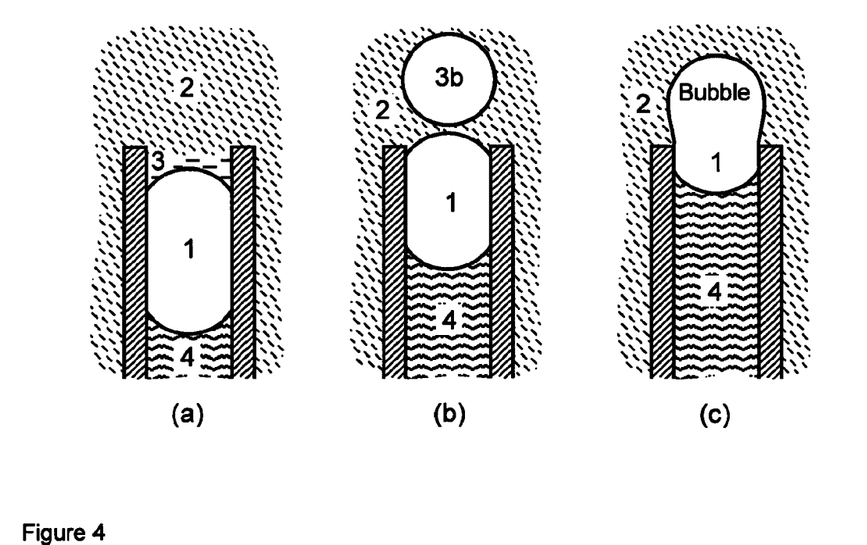

This procedure bases on the use of a gaseous inner phase. In FIG. 4 the procedure is illustrated. The aim is to quickly form a bubble large enough to be deformed at the tip of the capillary, so that ADSA can be used as a detection method. The inner volume of the system must be filled with a pure liquid without surfactant, (4) in FIG. 4. Then a small gas volume (0.1 to 100 microliters) is sucked through the capillary orifice. This gas will work as an inner phase (1). In the next step (not shown in FIG. 4) a plug (single or composite) protecting the bubble can be formed in the capillary as previously described in step (a) in procedure A. After that the capillary is dipped into a cuvette containing the outer phase, FIG. 4a. Then, pressure is applied by the injection module, (6) in FIG. 1. The plug (3) is rapidly pushed out. The injection module continues to drive the inner liquid until part of the gaseous inner phase is released as one or more bubbles, (3b) in FIG. 4b (In the figure the released bubble is denoted with (3b) as it could otherwise be considered as part of the protecting plug). The residue forms a bubble at the capillary tip (see FIG. 4c). The surface tension determination is realized by ADSA.

It is difficult to control the volume of a bubble when the bubble is part of a large volume of inner phase. The new feature of the method is that the volume of the inner gaseous phase is purposely as small as possible. This has two favorable consequences: (i) when the volume is very small, the bubble is much less deformable and its control is easier than it is when using large volume of air; (ii) besides the bubble volume does not change for many minutes and hours after the formation. Thus the determination of the ST does not require a complicated device (as in [8]) for keeping the bubble volume constant. The simpler procedure and device allow measuring the dynamic ST by ADSA within less than 100 milliseconds after bubble formation, which transforms ADSA in a method for studying rather fast adsorption processes.

In the implementation of the methods A and B, one can use a clean liquid filling of the major part of the inner volume (4), as in PBM. Thus the quantity of the inner phase (1) can be minimized to some microliters.

With the proposed device, already known methods can also be realized.

Stopped Jet Method (SJM).

A simplified preliminary version known under a different name ("Fast Formed Drop Technique"), was developed in 1999 [17, 18]. The main idea of the method is to use a jet of the inner phase in the outer phase to provide a pure interface. After stopping the jet, a drop remains at the capillary tip and the dynamic ST/IFT is calculated by means of the CPM. The main shortcomings of the device described in ref. [17,18] are the lack of any record of the drop evolution vs. time and the restriction to spherical drops. An improved version of SJM with respect to ref. [17,18] can be realized with the device described in FIG. 1:

(a) Electronic control of the entire process is implemented, which includes:
  automatic calibration of the parameters included in the calculation by CPM;
  by means of the electronics and injection module, (10) and (6) in FIG. 1, the jet velocity (0.1 m/s to 10 m/s) and duration (0.01 to 10 s) can be varied to reach suitable conditions for fast and smooth formation of the desired drop at the capillary tip: spherical or deformed;
  recording of the pressure and image data;
  automatic calculation of the dynamic ST/IFT.
(b) Preliminary selection of the conditions for fast mechanical relaxation. After stopping the jet, the device and the drop relax, which can be seen as damped oscillations of the pressure signal and the drop shape. These processes decrease the accuracy of the measured ST/IFT. This can be avoided by choosing suitable values of the elastic and damping properties of the device, the properties of the investigated fluids, and the conditions of the measurement.
c) Determination of the real surface age and synchronization between pressure and video data. The surface age is important for a correct interpretation of the ST/IFT data. To get a better defined moment of the new surface formation a video camera with 200 fps or more is used. For the synchronization between the pressure and the video data an electrical impulse from the driver of the motorized syringe at the beginning of the motion is applied. This impulse serves as a common start for acquisition sequences of the pressure signal and the video camera. These sequences are characterized by defined time intervals (e.g. 1 ms for the analog to digital conversion of the pressure signal and 5 ms for the image frames), which allow precise matching of their time axis. For eliminating the blur of the drop images, a short exposure time (e.g. 0.01 to 1 ms) is used—either by stroboscopic illumination or by camera electronic shutter.

The ST/I FT determination is performed by using SPM for spherical drops or by ADSA for deformed drops.

Drop Volume Method (DVM).

This method consists of forcing the inner liquid phase into the outer liquid phase through the capillary with a precisely formed tip [2]. When the growing drop reaches a given volume, which is determined by the equilibrium between the gravity and capillary forces, it detaches. Depending on the properties of the liquid/liquid system and the flow rate the drops detach at a particular frequency. The precisely determined volume of the detached drop is used to calculate the IFT. In popular commercial realizations of the DVM the detachment of the drop is detected by optical barrier (e.g. DVT30 by Krüss, GER).

Illustrative results obtained by the proposed methods are given on FIGS. 5 to 8.

Figure 5:
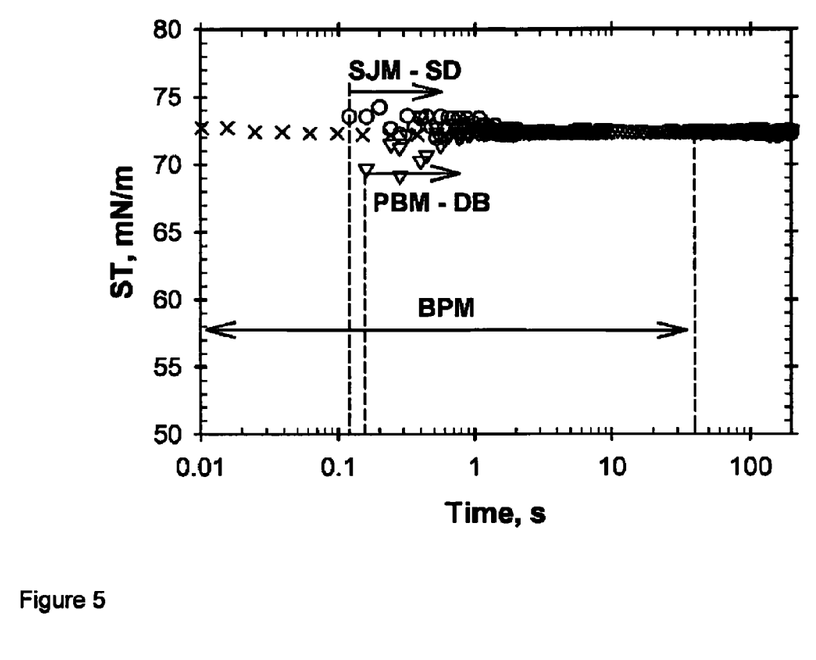
FIG. 5 Surface tension for clean water-air interface, measured by PBM-DB, BPM and SJM-SD.

Because of the presence of transient processes preceding the drop/bubble formation checks of the time dependence of the ST of pure water with different methods have been performed, see FIG. 5. The horizontal arrows indicate the time span after the drop formation after which correct values of the ST are obtained. ST measurement by PBM and SJM can start 0.1-0.2 s after the surface formation. For PBM, slight bubble oscillations are observed in the next 0.2-0.4 s. For comparison results obtained by the Bubble Pressure Method (BPM) are shown. The BPM has a small initial time, but it is limited at longer times due to the difficult control of the relatively large volume of the gas phase that is inherent to the method, see FIG. 5.

Figure 6:
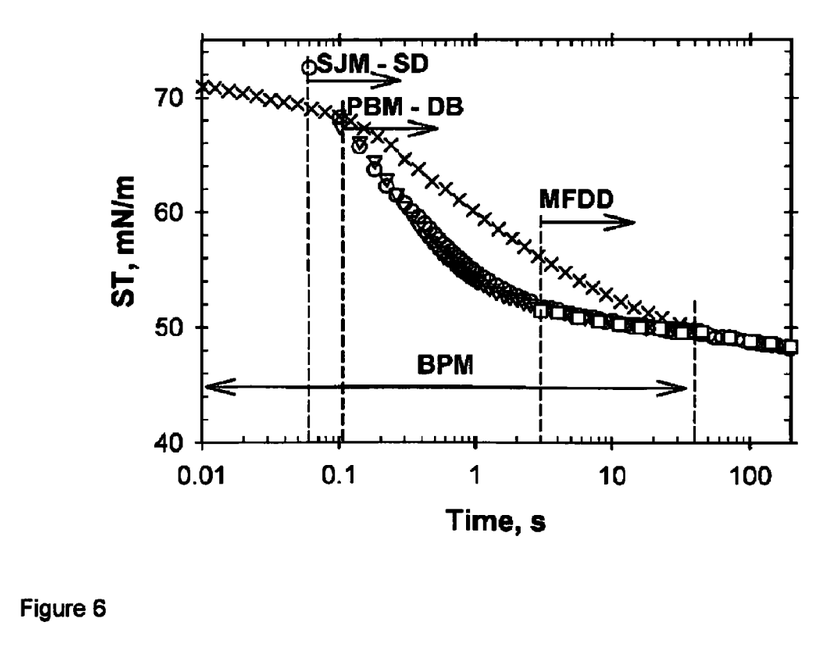
FIG. 6: Dynamic surface tension of surfactant solution—air interface, measured by BPM, SJM-SD, PBM-DB and MFDD.

In FIG. 6 the methods are compared to the Bubble Pressure Method (BPM) and to a manually formed deformed drop (MFDD, i.e. the operator expands a drop until it reaches a desired volume and/or shape) with surfactant solution (0.24 mM sodium dodecyl sulfate with 150 mM NaCl). The horizontal arrows again indicate the time span after the drop formation after which correct values of the ST are obtained. The main conclusions are: (i) all methods, except BPM, give coinciding results which after 3 seconds merge with the results of MFDD; (ii) the comparison of FIG. 6 with FIG. 5 shows that the initial times after which reliable values are obtained are shorter than for pure water (for the systems shown they are 60 ms for SJM-SD vs. 120 ms for pure water, for PBM-DB 100 ms vs. 200 ms for pure water). The observed discrepancy with BPM data is due to peculiarities of the BPM related to the fact that the surface of the bubble does not expand constantly but continuously [20].

Figure 7:
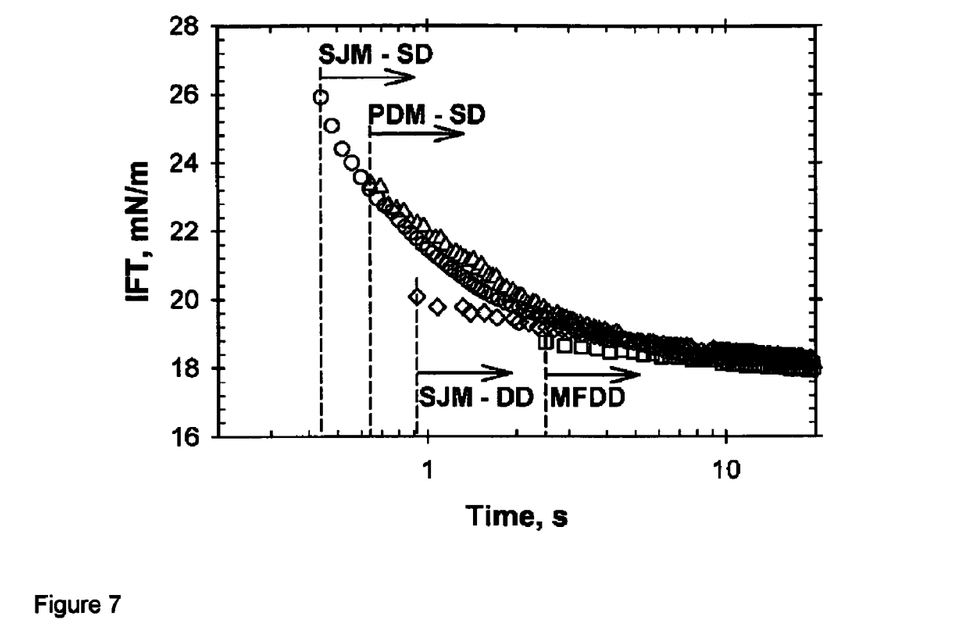
FIG. 7: Dynamic interfacial tension of surfactant solution—oil interface, realized by PDM-SD, SJM-SD, SJM-DD and MFDD.
Figure 8:
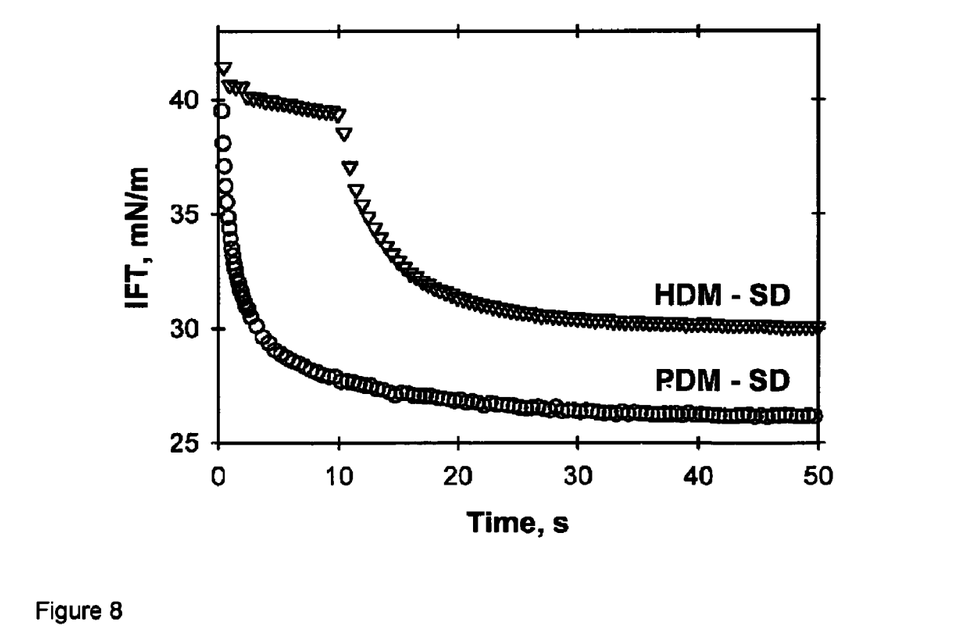
FIG. 8: Comparative plot for time dependences of the IFT for HDM-SD and PDM-SD.

Similar checks were performed for the IFT of 5 cP silicone oil/aqueous solution of 0.24 mM sodium dodecyl sulfate with 150 mM NaCl. The results for PDM-SD, SJM-SD, and SJM-DD vs. MFDD are shown in FIG. 7. The initial times are larger than for air-water surface on FIG. 6 because of the larger viscosity of the silicone oil, which decreases the speed of formation of the drop. FIG. 8 shows typical data for time dependence of the IFT for PBM and HDM. The plug remaining between the drop and the outer phase in the case of HDM decelerates the surfactant adsorption and the IFT begins to decrease, after a lag time, from the value of the pure oil/water interface to that of the equilibrium value with surfactant.

References

1. *Novel methods to study interfacial layers*, D. Mobius and R. Miller eds., Elsevier, Amsterdam, 2001.
2. *Drops and bubbles in interfacial research*, D. Mobius and R. Miller eds., Elsevier, Amsterdam, 1998.
3. *Dynamics of adsorption at liquid interfaces: Theory, Experiment, Application*, S. S. Dukhin, G. Kretzschmar and R. Miller eds., Elsevier, Amsterdam, 1995.
4. Adamson, A. W., Gast, A. P. *Physical Chemistry of Surfaces*, Wiley, New York, 6th edition, 1997.
5. Rotenberg, Y., Boruvka, L., Neumann, A. W. "Determination of surface tension and contact angle from the shapes of axisymmetric fluid interfaces" *J. Colloid Interface Sci.* 1983, 93, 169-181.
6. Cheng, P., Li, D., Boruvka, L., Rotenberg, Y., Neumann, A. W. "Automation of axisymmetric drop shape analysis for measurements of interfacial tensions and contact angles" *Colloids Surfaces* 1990, 43, 151-167.
7. Lin, S. Y.; McKeigue, K.; Maldarelli, C. "Diffusion-controlled surfactant adsorption studied by pendant drop digitization", *AIChE J.* 1990,36,1785-1795.
8. Cascao Pereira, L. G., Theodoly, O., Blanch, H. W. Radke, C. J., "Dilatational Rheology of BSA Conformers at the Air/Water Interface" *Langmuir* 2003, 19, 2349-2356.

9. Song, B., Springer, J. "Determination of interfacial tension from profile of a pendant drop using computer-aided image processing. 2. Experimental" *J. Colloid Interface Sci.* 1996, 184, 77-91.
10. Hoorfar, M., Neumann, A. W. "Recent progress in Axisymmetric Drop Shape Analysis (ADSA)" *Adv. Colloid Interface Sci.* 2006, 121, 25-49.
11. Passerone, A., Liggieri, L., Rando, M., Ravera, F., Ricci, E., "A new experimental method for measurement of the interfacial tension between immiscible fluids at zero Bond number", *J. Colloid Interface Sci.* 1991, 146, 152-162.
12. Horozov, T., Danov, K., Kralchevsky, P. A., Ivanov, I. B., Borwankar, R. "A local approach in interfacial rheology: Theory and experiment" Proc. First World Congress in Emulsion, Paris, 1993.
13. Wantke, K.-D., Lunkenheimer, K., Hempt, C., "Calculation of the elasticity of fluid boundary phases with the oscillating bubble method" *J. Colloid Interface Sci.*, 1993, 159, 28.
14. MacLeod, C. A., Radke, C. J., "Dynamic Surface Tension Measurements Using a Growing Drop Technique" J. Colloid Interface Sci. 1993, 160, 435-448.
15. Nagarajan, R., Wasan, D. T. "Measurement of dynamic interfacial tension by an expanding drop tensiometer" J. Colloid Interface Sci. 1993, 159, 164-173.
16. Zhang, X., Harris, M. T., Basaran, O. A. "Measurement of dynamic surface tension by a growing drop technique" J. Colloid Interface Sci. 1994, 168, 47-60.
17. Horozov, T., Arnaudov, L. "A Novel Fast Experimental Technique for Measuring Dynamic Surface and Interfacial Tension of Surfactant Solutions at Constant Interfacial Area", *J. Colloid and Interface Sci.* 1999, 219, 99-109.
18. Horozov, T., Arnaudov, L. "Adsorption Kinetics of Some Polyethylene Glycol Octylphenyl Ethers Studied by the Fast Formed Drop Technique", *J. Colloid Interface Sci.* 2000, 222, 146-155.
19. Method and Device for the Determination of Liquid-Liquid and Liquid-Gas Interfacial Properties, Patent application 10 2004 040 336.8, Aug. 12, 2004, Krüss GmBH.
20. N. C. Christov, K. D. Danov, P. A. Kralchevsky, K. P. Ananthapadmanabhan, A. Lips, The Maximum Bubble Pressure Method: Universal Surface Age and Transport Mechanisms in Surfactant Solutions. Langmuir 22 (2006) 7528-7542.

What is claimed is:

1. A method for the formation of fluid interfaces between an inner and an outer phase comprising: the inner and outer phases are initially separated by a fluid plug, which is pushed into the outer phase by a manual or automated dosing device and the fluid plug comprises at least one liquid.

2. A method according to claim 1 wherein, the plug is only partially pushed out and the rest remains as a diffusion buffer for any solute in the outer phase.

3. A method according to claim 2, wherein, the inner phase may consist of a gas or liquid volume, which is different from the liquid in the dosing device, and which may be protected either by a composite plug or by a single fluid plug from the outer phase, and is pushed out by means of a manual or automated dosing device.

4. A method according to claim 3, wherein, the formed interface is used for measurement of the dynamic surface/interfacial tension.

5. A device for realization of the method described in claim 1, wherein, a decreased pressure in the inner phase, created by an injection module, is used to suck fluids into the capillary to form the plug or to push out the inner phase with the plug by creating an increased pressure in the inner phase until a curved interface with the fluid of the outer phase is formed.

6. A device according to claim 5, wherein, an optical device consisting of a transmitted light illumination system and an optical detection system is used to determine the shape of the fluid interface in order to calculate the value of the surface/interfacial tension by using the Young-Laplace equation for a deformed or a spherical drop/bubble.

7. A device according to claim 6, wherein, a pressure detector is connected to measure the pressure difference between the inner phase and the outer phase in order to determine the capillary pressure across the interface and to calculate the ST/IFT by using the Young-Laplace equation.

8. A device according to claim 7, wherein, an electronic synchronization between the creation of the surface/interface, the pressure measurement and the drop shape detection is applied to determine the moment of surface formation with an accuracy in time measurement lower that than 2 seconds.

9. A device according to claim 8, wherein, the plug movement is programmed and controlled to allow the formation of a spherical or deformed drop at the capillary tip, and the drop shape is recorded for calculating the ST/IFT by using the Young-Laplace equation.

* * * * *